(12) United States Patent
Titen

(10) Patent No.: US 9,687,378 B1
(45) Date of Patent: Jun. 27, 2017

(54) SYSTEM FOR ALIGNING SHOULDERS FOR SPORTS TRAINING

(71) Applicant: Edward M. Titen, Tampa, FL (US)

(72) Inventor: Edward M. Titen, Tampa, FL (US)

(73) Assignee: LJR Business Consultants, Inc., Tampa, FL (US)

( * ) Notice: Subject to any disclaimer, the term of this patent is extended or adjusted under 35 U.S.C. 154(b) by 0 days.

(21) Appl. No.: 15/166,423

(22) Filed: May 27, 2016

Related U.S. Application Data

(60) Provisional application No. 62/326,053, filed on Apr. 22, 2016.

(51) Int. Cl.
*A61F 5/02* (2006.01)

(52) U.S. Cl.
CPC ...... *A61F 5/026* (2013.01); *A61F 2250/0007* (2013.01)

(58) Field of Classification Search
CPC .................................. A61F 5/026; A61F 5/37
USPC ....... 119/712, 713, 725, 751, 752, 756, 769, 119/770, 792, 850, 856, 857
See application file for complete search history.

(56) References Cited

U.S. PATENT DOCUMENTS

| | | | | |
|---|---|---|---|---|
| 637,156 A * | 11/1899 | Potts | ................ | A61F 5/028 2/44 |
| 796,623 A * | 8/1905 | Bailey | ................ | A61F 5/026 2/45 |
| 2,973,050 A * | 2/1961 | Bennett | ................ | F01L 1/00 180/286 |
| 4,173,973 A * | 11/1979 | Hendricks | ................ | A61F 5/024 602/19 |
| 5,685,831 A * | 11/1997 | Floyd | ................ | A61F 5/026 2/45 |
| 5,840,051 A * | 11/1998 | Towsley | ................ | A61F 5/0125 2/44 |
| 6,206,787 B1 * | 3/2001 | Kleppen | ................ | A63B 69/0059 473/207 |
| 2007/0156074 A1 * | 7/2007 | Cojbasic | ................ | A61F 5/026 602/19 |
| 2012/0252609 A1 * | 10/2012 | Gates | ................ | A63B 60/02 473/519 |
| 2015/0094633 A1 * | 4/2015 | Garcia | ................ | A61F 5/026 602/19 |

* cited by examiner

*Primary Examiner* — Tarla Patel
(74) *Attorney, Agent, or Firm* — Dunlap Bennett & Ludwig PLLC

(57) ABSTRACT

A hands-free shoulder and back/spine support device for facilitating the correct posture and alignment of the shoulders and back/spine of a wearer comprising at least one elongate base member having opposed free ends, the at least one elongate base member being adapted for overlying the upper back such that the opposed free ends thereof align with and extend to the approximate midpoints of the shoulders of the wearer, and strap members for securing the at least one elongate base member on the back of the wearer such that the shoulders of the wearer are maintained in a desired alignment for use with an athletic training system.

12 Claims, 4 Drawing Sheets

SYSTEM FOR ALIGNING SHOULDERS FOR SPORTS TRAINING

CROSS-REFERENCE TO RELATED APPLICATION

This application claims the benefit of priority of U.S. provisional application No. 62/326,053, filed Apr. 22, 2016, the contents of which are herein incorporated by reference.

BACKGROUND OF THE INVENTION

Proper shoulder alignment is critically important for activities such as, for example, golf, tennis, baseball, lacrosse, weight lifting, swimming, and the like. Currently available athletic training systems for these sports do not provide hands-free means for maintaining the shoulders and Back/Spine Angle in proper alignment while performing the required exercises.

SUMMARY OF THE INVENTION

One embodiment of the invention relates to a hands-free shoulder support device for facilitating the correct posture and alignment of the shoulders and Back/Spine of a wearer comprising at least one elongate base member having opposed free ends, wherein the at least one elongate base member is adapted for overlying the upper back such that the opposed free ends thereof align with and extend at least to the approximate midpoints of the shoulders of the wearer; and the device is provided with strap members for securing the at least one elongate base member on the back of the wearer such that the shoulders of the wearer are maintained in a desired alignment for use with an athletic training system.

An additional embodiment of the invention concerns a hands-free shoulder and back/spine support device as described above additionally comprising a second elongate base member adapted for overlying the spine and lower back of the wearer and matching the spine angle, and the elongate base members are adapted for assembly crosswise at the approximate midpoints between the opposed free ends thereof.

These and other features, aspects and advantages of the present invention will become better understood with reference to the following drawings, description and claims.

DETAILED DESCRIPTION OF THE INVENTION

Figure 1:
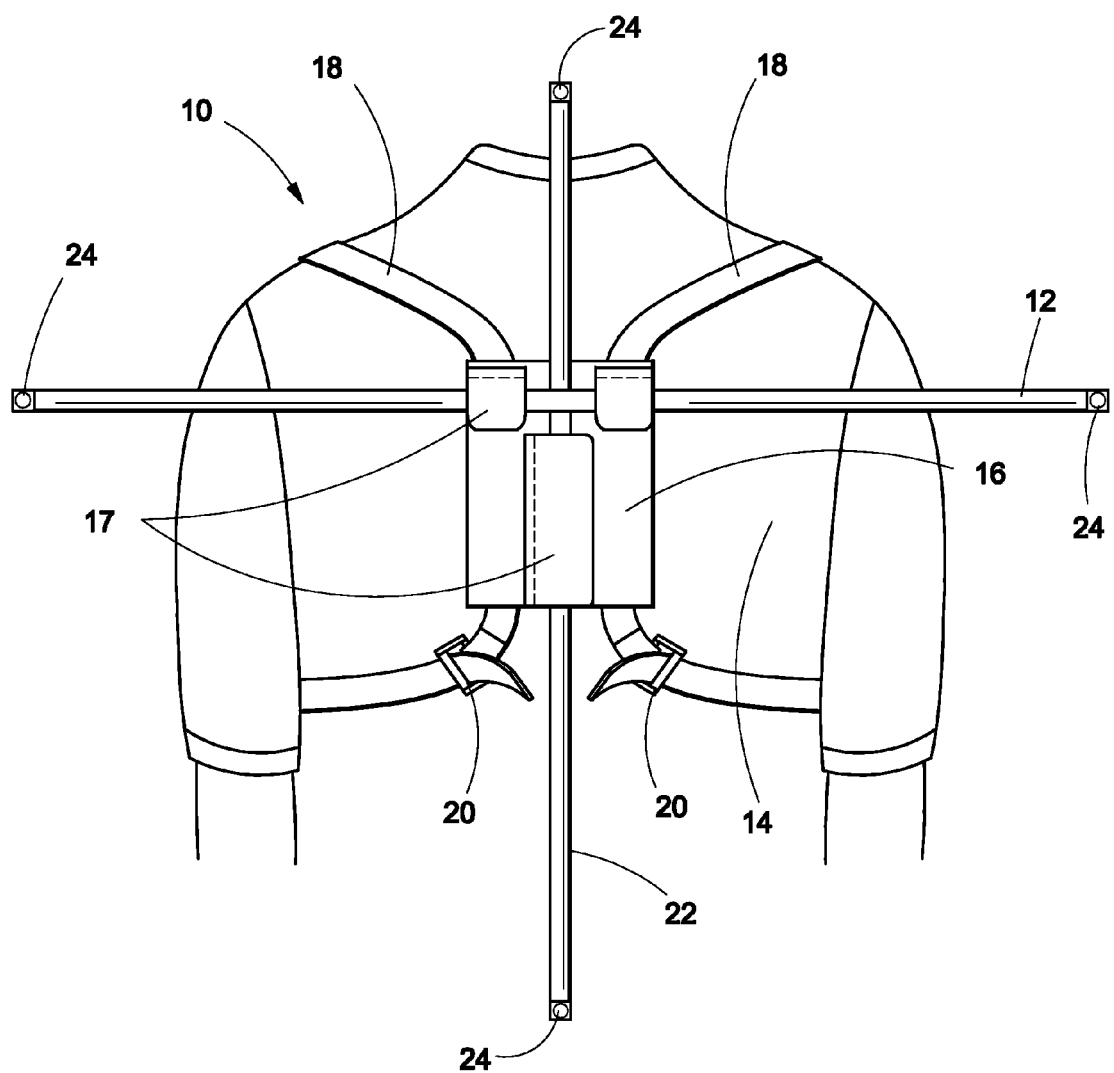
FIG. 1 is a perspective rear elevational view of the shoulder and back/spine support device positioned on a wearer.
Figure 2:
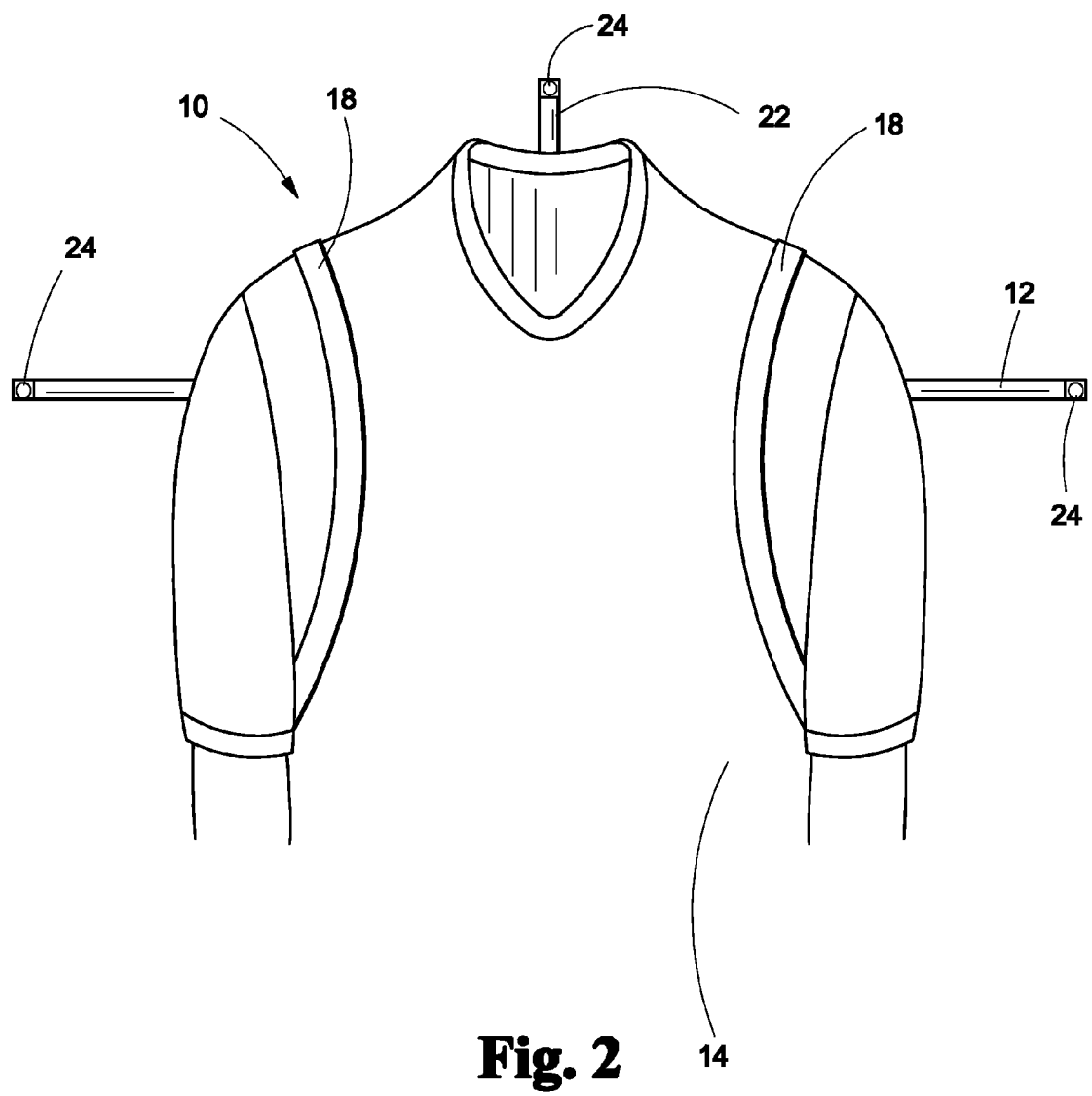
FIG. 2 is a perspective front elevational view of the shoulder support and back/spine device positioned on a wearer.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, the present invention provides a hands-free shoulder and back/spine alignment support device for facilitating the correct posture and alignment of the shoulders and back/spine of a wearer for use with an athletic training system.

Turning first to FIGS. 1-4, a detailed description concerning the present invention will first be provided. This description will then be followed by detailed explanation concerning use of the present invention.

As can be seen in those Figures, the shoulder support device 10 generally comprises an elongate primary shoulder rod 12 adapted to be positioned on the upper back of a wearer 14 and held in place by holder 16, which is secured on the back of wearer 14 by straps 18 having first and second opposed ends, the first end of each shoulder strap member being secured to the elongate base member adjacent the spine support area, and the second end of each of the shoulder strap members being secured to an intermediate portion of the elongate base member such that the second end of each of the shoulder strap members is located to communicate with an arm pit of the wearer, during use, without either the first or the second shoulder strap member overlapping one another or a spine of a wearer during use of the shoulder and back/spine support and alignment device. The straps 18 are provided with length adjusting clips 20.

An optional second elongate vertically disposed rod 22 may be positioned in holder for alignment along the spine of wearer 14.

Optional tracking lights, electronic sensors or computer trackers 24 may be positioned on the opposed ends of the shoulder rod 12 and/or the opposed ends of the back/spine rod 22.

Figure 3:
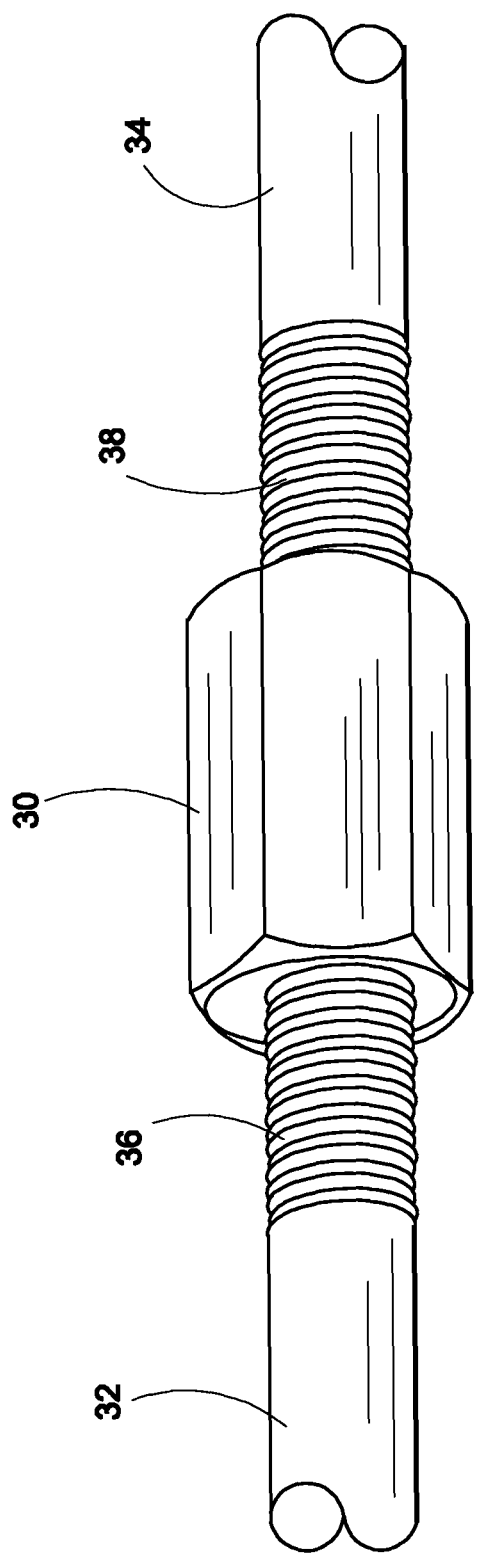
FIG. 3 is a perspective side elevational view of a connector of elements of the shoulder support device.

Alternatively, as depicted in FIG. 3, the rods may comprise a connector 30, into which elements 32 and 34 of the rod are secured by male and female threaded ends 36 and 38, or the unitary rod 12 is simply slid through a non-threaded connector.

Figure 4:
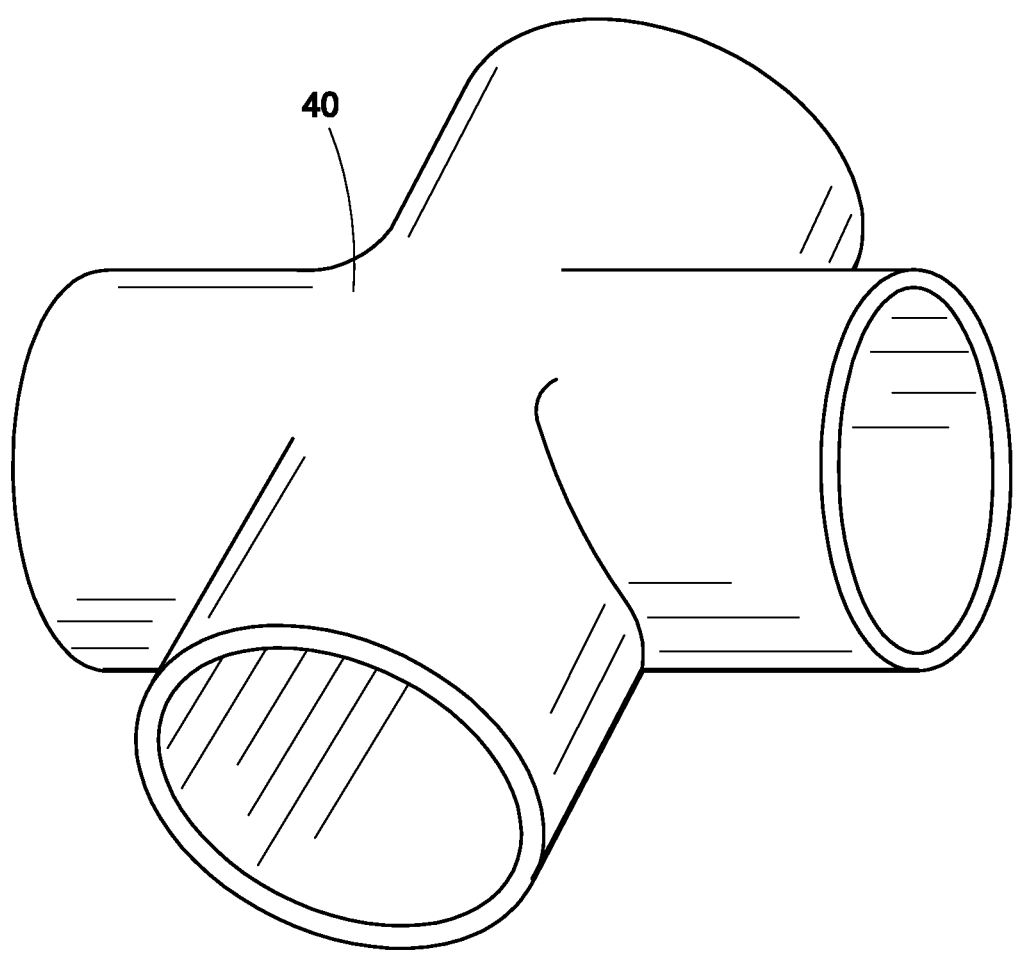
FIG. 4 is a perspective side elevational view of a second connector of elements of the shoulder support device.

In addition, as shown in FIG. 4, rather than being positioned on the back of the wearer 14 by holder 16, the elements of the shoulder and vertical rods may be secured by a cross-connector 40, into which elements of both rods are secured by male and female threaded ends.

It will be apparent to those skilled in the art that the rods, holder, connectors, straps and length adjusting clips of the shoulder support device of the invention may be constructed of any conveniently available material suitable for the purpose.

Preferably, the rods are constructed of sufficiently rigid material to maintain alignment of the shoulders and back/spine during use. Exemplary of such construction materials are wood, rigid plastics such as Callaway Alignment Stix, Maxfli Collapsible Alignment Sticks, and MVP Sport Leadbetter Golf Alignment Sticks, and metals such as aluminum, for example.

Suitable materials for constructing the straps include elastic polymers such as, for example, Stretchrite Heavy Duty Elastic White, Stretchrite Knit Elastic Heavy Stretch, Conrad Jarvis Heavy Duty Knit Elastic, Strapworks Elastic Bands, and the like.

The holder may be constructed of leather or any suitable fabric such as, for example, nylon, carbon Fiber, Denier Polyester, Denier Nylon, Synthetic Leather, and the like. In addition, the holder is preferably provided with Velcro closures 17 to facilitate positioning and removal of the elongate rods.

In operation, after inserting the rod or rods in the material pouch or any of the depicted connectors, the user then places their arms through the elastic straps as if they were donning a coat. The straps are then adjusted with the provided clips to make the rods parallel and vertical with the shoulders and spine to permit correct training with the shoulders and/or back/spine angle properly aligned, hands free.

Typically, the device of the invention may be manufactured by attaching 4+/−1½ inch wide elastic straps to a +/−4 inch by +/−8 inch leather or semi rigid fabric. Two straps on each side of the 4×8 inch material are connected with an adjustable clip. Additional material and Velcro are attached to the 4×8 inch material so as to create a pouch pocket to hold one rod in a horizontal position and one rod in a vertical position.

Alternatively, as depicted in the remaining drawings, metallic rods fabricated from aluminum, for example, and provided with male and female threaded ends could be joined to form a cross, similar to the American Red Cross symbol or a Greek cross.

In still another embodiment, the threaded rods could be inserted into a common cross connector as depicted in the drawing.

It should be understood, of course, that the foregoing relates to exemplary embodiments of the invention and that modifications may be made without departing from the spirit and scope of the invention as set forth in the following claims.

What is claimed is:

1. A hands-free shoulder alignment indicator for use with an athletic training system configured to indicate a posture and an alignment of a wearer's shoulders and back/spine during an athletic movement comprising:
    a substantially rigid horizontal member having unrestrained opposed free ends, wherein the horizontal member is adapted for overlying an upper back of the wearer such that the opposed free ends thereof align with and extend beyond the shoulders of the wearer;
    a substantially rigid vertical member having unrestrained opposed free ends, adapted for overlying the back/spine of the wearer; and
    a holder for securing the horizontal member and the vertical member in a fixed orthogonal orientation relative each other; and
    a strap configured to maintain the holder centered on the back of the wearer between the wearer's shoulders such that the shoulder alignment of the wearer is indicated by the opposed free ends of the horizontal member extending beyond the wearer's shoulder and the back/spine alignment of the wearer is indicated by the opposed free ends of the vertical member during the wearer's performance of the athletic movement.

2. The hands-free shoulder alignment indicator of claim 1, additionally comprising and the horizontal and vertical members are adapted for assembly crosswise at an approximate midpoints between the opposed free ends thereof.

3. The hands-free shoulder alignment indicator of claim 1, additionally comprising:
    a holder for holding the vertical member and strap.

4. The hands-free shoulder alignment indicator of claim 3, wherein said holder is a pouch.

5. The hands-free shoulder alignment indicator of claim 3, wherein said holder is a connector provided with male and female threaded elements.

6. The hands-free shoulder alignment indicator of claim 2, additionally comprising an element for holding the horizontal and vertical members and strap.

7. The hands-free shoulder alignment indicator of claim 6, wherein said holder is a pouch.

8. The hands-free shoulder alignment indicator of claim 6, wherein said holder is a connector provided with male and female threaded elements.

9. The hands-free shoulder alignment indicator of claim 1, wherein said vertical member is constructed of aluminum.

10. The hands-free shoulder alignment indicator of claim 1, wherein said strap is constructed of an elastic material.

11. The hands-free shoulder alignment indicator of claim 1, wherein said strap is provided with length adjusting clips.

12. The hands-free shoulder alignment indicator of claim 1, wherein said horizontal member is provided with tracking lights at the opposed free ends.

\* \* \* \* \*